United States Patent [19]

Martin

[11] Patent Number: 4,720,566
[45] Date of Patent: Jan. 19, 1988

[54] METHOD AND COMPOSITION FOR INHIBITING ACRYLONITRILE POLYMERIZATION

[75] Inventor: John F. Martin, Conroe, Tex.

[73] Assignee: Betz Laboratories, Inc., Trevose, Pa.

[21] Appl. No.: 922,378

[22] Filed: Oct. 23, 1986

[51] Int. Cl.$^4$ ............................................. C07C 121/32
[52] U.S. Cl. ..................................................... 558/306
[58] Field of Search ......................................... 558/306

[56] References Cited

U.S. PATENT DOCUMENTS

| | | | |
|---|---|---|---|
| 2,758,131 | 8/1956 | Couvillon | 558/306 |
| 3,428,666 | 2/1969 | Schneider et al. | 558/306 |
| 3,689,558 | 9/1972 | Modeen et al. | 564/127 |
| 4,267,365 | 5/1981 | Findeisen | 560/205 |
| 4,673,489 | 6/1987 | Roling | 208/289 |

FOREIGN PATENT DOCUMENTS 40-7172  4/1965  Japan .................................. 558/306

OTHER PUBLICATIONS

The Merck Index, 10th Ed., (1983), p. 6423.

Primary Examiner—Joseph Paul Brust
Attorney, Agent, or Firm—Alexander D. Ricci; Bruce E. Peacock

[57] ABSTRACT

This invention relates to compositions and methods of inhibiting acrylonitrile polymerization, particularly in quench columns of systems producing acrylonitrile, comprising adding to the acrylonitrile an effective amount for the purpose of (a) a hydroxylamine having the formula

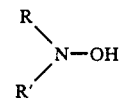

wherein R and R' are the same or different and are hydrogen, alkyl, aryl, alkaryl or aralkyl groups, and (b) a para-phenylenediamine or derivative thereof having at least one N—H group. Preferably the phenylenediamine is a para-phenylenediamine having the formula

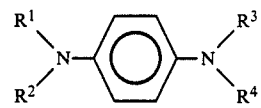

wherein $R^1$, $R^2$, $R^3$ and $R^4$ are the same or different and are hydrogen, alkyl, aryl, alkaryl, or aralkyl groups with the proviso that at least one of $R^1$, $R^2$, $R^3$ or $R^4$ is hydrogen.

6 Claims, No Drawings

METHOD AND COMPOSITION FOR INHIBITING ACRYLONITRILE POLYMERIZATION

BACKGROUND OF THE INVENTION

This invention relates to a composition and method for use in inhibiting acrylonitrile polymerization, particularly in quench columns of acrylonitrile producing systems.

Acrylonitrile is commercially produced in systems with the Sohio process. In a commercial acrylonitrile system utilizing this process, the reactor feeds are propylene, ammonia and compressed air. The propylene and ammonia are vaporized, then combined with the air and fed to a fluidized bed catalytic reactor. Precise ratios of the three feeds are maintained for optimum yield. The catalyst in the reactor vessel is a powder, which is maintained in a turbulent fluid state through the velocity of the air feed. The three mix together in the reactor and react on the surface of the fluidized catalyst. A set of complex exothermic reactions takes place, thereby forming the following products: acrylonitrile, hydrogen cyanide, carbon dioxide, carbon monoxide, acetonitrile, acrolein, acrylic acid, water, other higher nitriles, aldehydes, ketones, acetic acid and a number of miscellaneous unknown organic compounds. Conversion of the three feeds is less than 100%, thus unreacted propylene, ammonia, oxygen and nitrogen are contained in the reactor effluent gas. A portion of the heat of the exothermic reaction is removed by sets of steam coils which generate and superheat waste steam at approximately 600 psig. Reactor effluent gas passes through cyclones, which remove catalyst fines from the gas. The gas is then further cooled in a reactor effluent cooler, which is comprised of a shell and tube exchanger using boiler feedwater as the cooling source.

As the gas leaves the reactor effluent cooler, it then enters a quench column. The quench column cools the reactor effluent by contacting it with a recirculating water stream. Most of the water vapor and small amounts of organic vapors in the reactor effluent are condensed in the quench column. The quench column bottoms are cooled and circulated back to the quench column. The quench column can contain internal trays or packing to provide intimate contact of upflowing gas with downflowing water. Sulfuric acid is injected into the recirculating quench water to neutralize unreacted ammonia in the reactor effluent. The excess quench water is roughly equal to the amount of water produced by the reactor and is fed to the wastewater column where acrylonitrile and hydrogen cyanide are recovered. Wastewater column bottoms are cooled and neutralized, mixed with other plant waste streams, clarified and injected into the wastewater injection well.

The quench column effluent gas is then directed to an absorber where chilled water is used to absorb acrylonitrile, hydrogen cyanide and other organics from the gas. Absorber bottoms are fed to a recovery column where a crude acrylonitrile product is taken overhead. The crude acrylonitrile product is then purified using a series of distillation columns, referred to as the purification section. The first column (heads column) removes hydrogen cyanide, while the second column (drying column) removes water. The last column (product column) takes a pure acrylonitrile monomer product from a side-draw near the top of the column. Heavy ends are rejected from the product column bottoms.

The acrylonitrile can polymerize in the quench column. More specifically, as the reactor effluent gas is passed through the quench column, a portion of the acrylonitrile contained in the gas polymerizes and is absorbed into the recirculating quench water. The amount of acrylonitrile that polymerizes in the quench column represents an undesirable net product loss for the acrylonitrile plant. For example, in an uninhibited quench column, between about 2% to 5% of the total acrylonitrile produced by the reactor is lost due to polymerization in the quench column.

Known polymerization inhibitors for acrylates include phenothiazine, hydroquinone, the methyl ether of hydroquinone, benzoquinone, and methylene blue. Of primary interest is Japanese Patent No. 47-18820 which discloses the use of dialkylhydroxylamine of generic structure

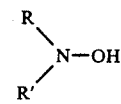

(with R and R' as its alkyl radicals), singly or together with other sundry polymerization inhibitors, to inhibit polymerization of unsaturated compounds of generic structure

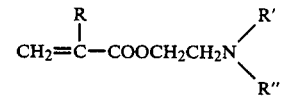

(where R stands for hydrogen or methyl radical and R' and R" for alkyl radicals). Also, May in U.S. Pat. No. 3,408,422 discloses a process for stabilizing ethylenically unsaturated polyesters and a composition stabilized against premature gelatin comprising (1) a hydroxy-containing ethylenically unsaturated polyester of a glycidyl polyether of a polyhydric phenol and an ethylenically unsaturated monocarboxylic acid, and (2) a hydroxylamine compound.

Phenylenediamines alone or with oxygen are known in the art as polymerization inhibitors in acrylate systems. Otsuki et al. in U.S. Pat. No. 3,674,651 discloses a process for inhibiting the polymerization of acrylic acid using a combination of diphenylamine or its derivatives and an oxygen-containing gas, or mixtures of diphenylamine or its derivatives with benzoquinone and/or hydroquinone mono-methyl-ether and an oxygen-containing gas. Wilder, in U.S. Pat. No. 4,016,198, discloses a method of inhibiting polymerization of unsaturated carboxylic acid esters and improved unsaturated carboxylic acid ester compositions comprising incorporating into the ester composition a combination of polyalkyleneamines and certain N-aryl-o or p-phenylenediamines. Also, Mullins in U.S. Pat. No. 4,017,544 discloses the use of a class of N-(nitroalkyl)-N'-phenyl-p-phenylenediamines to inhibit the polymerization of unsaturated carboxylic acid esters. Findeisen in U.S. Pat. No. 4,267,365 discloses a process for the preparation of certain oligomeric acrylic acids wherein the acrylic acid is heated in the presence of 0.001 to 1% by weight of a polymerization inhibitor consisting of molecular oxygen, nitric oxide, a phenol, a quinone, an aromatic amine, a nitro compound or diphenylpicrylhydrazyl to a temperature from about 50° to 200° C. Clonce et al. in U.S. Pat. No. 4,480,116 discloses an improved method for preparing and processing readily polymerizable acrylate monomers by employing phenyl-para-benzoquinone, 2,5-diphenyl-para-benzoquinone, or a mixture thereof. None of these prior art references recognizes the unique mixture of hydroxylamine and phenylenediamine or derivatives thereof having at least one N—H group as desirable for inhibiting acrylonitrile polymerization.

SUMMARY OF THE INVENTION

This invention relates to compositions and methods of inhibiting acrylonitrile polymerization comprising adding to the acrylonitrile an effective amount for the purpose of (a) a hydroxylamine having the formula

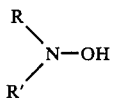

wherein R and R' are the same or different and are hydrogen, alkyl, aryl, alkaryl or aralkyl groups, and (b) a phenylenediamine or derivative thereof having at least one N—H group. Preferably, the phenylenediamine is a para-phenylenediamine having the formula

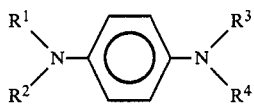

wherein $R^1$, $R^2$, $R^3$ and $R^4$ are the same or different and are hydrogen, alkyl, aryl, alkaryl, or aralkyl groups with the proviso that at least one of $R^1$, $R^2$, $R^3$ or $R^4$ are hydrogen. This mixture is particularly useful for inhibiting acrylonitrile polymerization in a quench column of an acrylonitrile plant, thereby allowing the plant to recover more acrylonitrile.

Accordingly, it is an object of the present invention to provide compositions and methods for inhibiting the polymerization of acrylonitrile. It is another object of this invention to provide methods and compositions for inhibiting acrylonitrile polymerization in a quench column of a system producing acrylonitrile. It is a further object of the present invention to provide economically effective acrylonitrile polymerization inhibiting compositions and methods. These and other objects and advantages of the present invention will be apparent to those skilled in the art upon reference to the following detailed description of the invention.

DETAILED DESCRIPTION OF THE INVENTION

The hydroxylamines used with phenylenediamine or derivatives thereof having at least one N—H group in accordance with the instant invention correspond to the chemical formula:

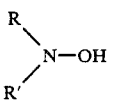

wherein R and R' are the same or different and are hydrogen, alkyl, aryl, alkaryl, or aralkyl groups. The alkyl, alkaryl and aralkyl groups may be straight or branched-chain groups. Preferably, the alkyl, aryl, alkaryl, or aralkyl groups have one to about twenty carbon atoms. Examples of suitable hydroxylamines include N,N-diethylhydroxylamine; N,N-dipropylhydroxylamine; N,N-dibutylhydroxylamine; N,N-butylethylhydroxylamine; N,N-2-ethyl-butryloctylhydroxylamine; N,N-didecylhydroxylamine; N,N-dibenzylhydroxylamine; N-benzylhydroxylamine; N,N-butylbenzylhydroxylamine; N-phenylhydroxylamine; N,N-butylphenylhydroxylamine; methylbenzylhydroxylamine; ethylbenzylhydroxylamine; etc. More than one such hydroxylamine, such as mixtures of benzylhydroxylamines and methylbenzylhydroxylamines, may be utilized if desired. Most preferably, the hydroxylamine is selected from the group consisting of N,N-diethylhydroxylamine, N,N-dibenzylhydroxylamine, methylbenzylhydroxylamine, and ethylbenzylhydroxylamine.

The phenylenediamine component of the inhibitor mixtures of this invention include phenylenediamine and derivatives thereof having at least one N—H group. It is thought that ortho-phenylenediamine or derivatives thereof having at least one N—H group are suitable for use in accordance with the instant invention. However, the preferred phenylenediamine is para-phenylenediamine having the formula

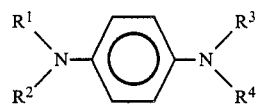

wherein $R^1$, $R^2$, $R^3$ and $R^4$ are the same or different and are hydrogen, alkyl, aryl, alkaryl, or aralkyl groups with the proviso that at least one of $R^1$, $R^2$, $R^3$ or $R^4$ is hydrogen. More preferably, the alkyl, aryl, alkaryl and aralkyl groups have one to about twenty carbon atoms. The alkyl, alkaryl and aralkyl groups may be straight or branched-chain groups. Exemplary para-phenylenediamines include p-phenylenediamine wherein $R^1$, $R^2$, $R^3$ and $R^4$ are hydrogen; N,N,N'-trialkyl-p-phenylenediamines, such as N,N,N'-trimethyl-p-phenylenediamine, N,N,N'-triethylphenylene-p-diamine, etc.; N,N-dialkyl-p-phenylenediamines, such as N,N-dimethyl-p-phenylenediamine, N,N-diethyl-p-phenylenediamine, etc.; N-phenyl-N',N'-dialkyl-p-phenylenediamines such as N-phenyl-N'-N'-dimethyl-p-phenylenediamine, N-phenyl-N',N'-diethyl-p-phenylenediamine, N-phenyl-N',N', -dipropyl-p-phenylenediamine, N-phenyl-N',N'-di-n-butyl-p-phenylenediamine, N-phenyl-N',N'-di-sec-butyl-p-phenylenediamine, N-phenyl-N'-methyl-N'-ethyl-p-phenylenediamine, N-phenyl-N'-methyl-N'-propyl-p-phenylenediamine, etc.; N-phenyl-N'-alkyl-p-phenylenediamines, such as N-phenyl-N'-methyl-p-phenylenediamine, N-phenyl-N'-ethyl-p-phenylenediamine, N-phenyl-N'-propyl-p-phenylenediamine, N-phenyl-N'-isopropyl-p-phenylenediamine, N-phenyl-N'-butyl-p-phenylenediamine, N-phenyl-N'-isobutyl-p-phenylenediamine, N-phenyl-N'-isobutyl-p-phenylenediamine, N-phenyl-N'-sec-butyl-p-phenylenediamine, N-phenyl-N'-tert-butyl-phenylenediamine, N-phenyl-N'-n-pentyl-p-phenylenediamine, N-phenyl-N'-n-hexyl-p-phenylenediamine, N-phenyl-N'-(1-methylhexyl)-p-phenylenediamine, N-phenyl-N'-(1,3-dimethylbutyl)-p-phenylenediamine, N-phenyl-N'-(1,4-dimethylpentyl)-p-phenylenediamine, etc. Preferably, the para-phenylenediamine is selected from the group consisting of N-phenyl-N'-(1,3-dimethylbutyl)-p-phenylenediamine, N-phenyl-N'-(1,4-dimethylpentyl)-p-phenylenediamine, and para-phenylenediamine wherein $R^1$, $R^2$, $R^3$ and $R^4$ are hydrogen.

The total amount of hydroxylamine and phenylenediamine or derivatives thereof having at least one N—H group used in the compositions and methods of the present invention as a polymerization inhibitor is that amount which is sufficient to effect inhibition of acrylonitrile polymerization and will, of course, vary according to the particular conditions under which it is used. At higher temperatures, larger amounts are generally required. Preferably, the total amount of hydroxylamine and phenylenediamine or derivatives thereof having at least one N—H group is from about 1 ppm to about 10,000 ppm based upon the weight of the acrylonitrile. Most preferably, the total amount of the aforesaid compounds is from about 1 ppm to about 1000 ppm based upon the weight of the acrylonitrile. The relative concentrations of hydroxylamine and phenylenediamine or derivatives thereof having at least one N—H group are generally in the range of about 5 to about 95 weight percent hydroxylamine and about 95 to about 5 weight percent phenylenediamine or derivatives thereof having at least one N—H group based on the total combined weight of these components. Preferably, the molar ratio of hydroxylamine to phenylenediamine or derivatives thereof having at least one N—H group is about 1:10 to about 10:1 and, most preferably, the molar ratio is about 1:5 to about 5:1.

The hydroxylamine and phenylenediamine or derivatives thereof can be provided to the acrylonitrile by any conventional method. The components can be added to the acrylonitrile as a single composition containing the inhibitor compounds or the individual components can be added separately or in any other desired combination. The composition may be added as either a concentrate or as a solution using a suitable carrier solvent which is compatible with the acrylonitrile.

The instant invention is useful as a process inhibitor, which is employed during the preparation and processing of acrylonitrile. Acrylonitrile is commercially produced in a system with the Sohio process, which is familiar to those skilled in the art. The Sohio process is disclosed in U.S. Pat. No. 2,904,580 (Idol). The entire disclosure of this patent is accordingly incorporated by reference. This process generally involves vaporizing propylene and ammonia and then combining these vaporized compounds with compressed air and feeding the mixture to a fluidized bed catalytic reactor. Precise ratios of the propylene, ammonia and compressed air are maintained for optimum yield. The catalyst in the reactor is a powder, which is maintained in a turbulent fluid state through the velocity of the air being fed into the reactor. Examples of catalysts which could be utilized include bismuth, tin and antimony salts of phosphomolybdic and molybdic acids and bismuth phosphotungstate. The propylene, ammonia and air mix together in the reactor and react on the surface of the fluidized catalyst. A set of complex exothermic reactions takes place in the reactor, thereby forming the following products: acrylonitrile, hydrogen cyanide, carbon dioxide, carbon monoxide, acetonitrile, acrolein, acrylic acid, water, other higher nitriles, aldehydes, ketones, acetic acid and other miscellaneous unknown organic compounds. Conversion of the propylene, ammonia and air is less than 100% and, therefore, unreacted propylene, ammonia, oxygen and nitrogen is contained in reactor effluent gas. The reactor effluent gas then passes through cyclones, which remove catalyst fines from the gas. The gas is then further cooled in a reactor effluent cooler, which is comprised of a shell and tube exchanger using boiler feedwater as the cooling source. As the gas leaves the reactor effluent cooler, it then enters a quench column. The quench column cools the reactor effluent gas by contact of the gas with a recirculating water stream. Most of the water vapor and small amounts of organic vapors in the reactor effluent gas are condensed in the quench column. The quench column bottoms are cooled and circulated back to the quench column. The quench column can contain internal trays or packing to provide intimate contact of upflowing gas with downflowing water. Sulfuric acid is injected into the recirculating quench water to neutralize unreacted ammonia in the reactor effluent gas. Excess quench water is roughly equal to the amount of water produced by the reactor and is fed to a wastewater column where acrylonitrile and hydrogen cyanide are recovered. Wastewater column bottoms are cooled and neutralized, mixed with other plant waste streams, clarified and injected into a wastewater injection well.

As the reactor effluent gas is passed through the quench column, a portion of the acrylonitrile contained in the gas polymerizes and is absorbed into the recirculating quench water. The amount of acrylonitrile that polymerizes in the quench column represents a net product loss for the acrylonitrile producing system. For example, in an uninhibited quench column, between about 2% to 5% of the total acrylontrile produced by the reactor is lost due to polymerization in the quench column. The polymerization of the acrylonitrile is believed to be initiated and accelerated by the presence of heat, ammonia, oxygen and peroxides.

Effluent gas from the quench column is thereafter directed to an absorber where chilled water is used to absorb acrylonitrile, hydrogen cyanide and other organics from the gas. Absorber bottoms are fed to a recovery column where a crude acrylonitrile product is taken overhead. The crude acrylonitrile product is then purified using a series of distillation columns, referred to as the purification section. The purification section includes: a first distillation column which removes hydrogen cyanide (heads column); a second distillation column (drying column), which removes water; and a third distillation column (product column), which takes a pure acrylonitrile monomer product from a side-draw near the top of the column.

The present invention is useful for inhibiting acrylonitrile polymerization in the quench column of a system producing acrylonitrile. Preferably, the hydroxylamine and para-phenylenediamine components of this invention are injected into the reactor effluent gas downstream of the reactor effluent cooler in the acrylonitrile producing system. By reducing the rate of acrylonitrile polymerization of the reactor effluent gas, additional amounts of acrylonitrile monomer pass through the quench column, thereby allowing the system to recover more acrylonitrile in the absorber and purification sections of the system.

TRIAL

A trial was conducted at a commercial acrylonitrile producing plant. An additive comprised of active ingredients 10 wt. % N-phenyl-N'-(1,3-dimethylbutyl)-p-phenylenediamine and 15 wt. % N,N-diethylhydroxylamine, and solvents 10 wt. % dimethylformamide and 65 wt. % heavy aromatic naphtha, was applied in the two quench columns of the plant by injection into the reactor effluent gas downstream of the reactor effluent coolers. The additive was injected into the gas using a pneumatic spray nozzle. The additive feedrate was 50 ppm (wt./wt.) for two days of pretreatment and 25 ppm (wt./wt.) during the remainder of the trial (10 days total). The additive feed-rate was based on reactor effluent gas flow.

Total carbon analyses were run on samples of wastewater column bottoms. The total carbon measures the amount of acrylonitrile polymers and other non-volatile hydrocarbons. In the untreated case, the total carbon as measured was between 59,000–60,000 pounds per day. In the treated case, the total carbon increased to an average of 65,000 pounds per day. The total carbon increase noted during the treated case was believed to be due to sloughage of previously formed acrylonitrile polymer from the quench column packing.

The effectiveness of the additive in inhibiting acrylonitrile polymerization was determined by measuring the change in acrylonitrile recovery efficiency. Two methods were used to monitor the recovery efficiency: a flow meter immediately upstream of two rundown tanks where the acrylonitrile product was stored (called Totalizer Recovery Efficiency), and actual inventory changes in the rundown tanks (called Co-op Recovery Efficiency). Both of the monitoring methods indicated recovery efficiency increased with additive treatment. The Totalizer Recovery Efficiency increased 2.0% (from an untreated average of 97.7% to a treated average of 99.7%), and the Co-op Recovery Efficiency increased 0.7% (from an untreated average of 97.2% to a treated average of 97.9%). This significant additional recovery of acrylonitrile monomer product indicates that acrylonitrile polymerization in the quench column was minimized by the addition of the additive in accordance with the present invention.

The inhibition reactions of the mixture of the present invention are believed to be by several mechanisms. The two active components of this invention react with hydrocarbon free radicals in the gases to terminate their activity. The mixture of this invention also terminates free radicals caused by ammonia as the ammonia initially condenses into water but before the ammonia is neutralized with sulfuric acid. Additionally, the hydroxylamine may scavenge a measured level of oxygen dissolved in the recirculating quench water (about 0.7 mg/L dissolved oxygen). The mixture of this invention also deactivates peroxy free radicals. The mixture, its reaction products, and its aforementioned compatible solvents are non-volatile at quench column operating conditions and will wind up in the wastewater column bottoms.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

What is claimed is:

1. A method of inhibiting acrylonitrile polymerization in a quench column of a system producing acrylonitrile comprising adding to the acrylonitrile an effective amount for the purpose of (a) a hydroxylamine having the formula

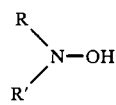

wherein R and R' are the same or different and are hydrogen, alkyl, aryl, alkaryl or aralkyl groups, and (b) a para-phenylenediamine having the formula

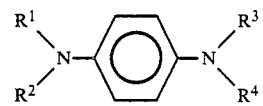

wherein $R^1$, $R^2$, $R^3$ and $R^4$ are the same or different and are hydrogen, alkyl, aryl, alkaryl, or aralkyl groups with the proviso that at least one of $R^1$, $R^2$ $R^3$, or $R^4$ is hydrogen, wherein: the alkyl, aryl, alkaryl and aralkyl groups have one to about twenty carbon atoms; the total amount of the hydroxylamine and the phenylenediamine is from about 1 ppm to about 10,000 ppm based upon the weight of the acrylonitrile; and the molar ratio of the hydroxylamine to the phenylenediamine is about 1:10 to about 10:1.

2. The method according to claim 1 wherein the hydroxylamine is selected from the group consisting of N,N-diethylhydroxylamine, N,N-dibenzylhydroxylamine, methylbenzylhydroxylamine, and ethylbenzylhydroxylamine.

3. The method according to claim 2 wherein the para-phenylenediamine is selected from the group consisting of N-phenyl-N'-(1,3-dimethylbutyl)-p-phenylenediamine, N-phenyl-N'-(1,4-dimethylpentyl)-p-phenylenediamine, and para-phenylenediamine wherein $R^1$, $R^2$, $R^3$ and $R^4$ are hydrogen.

4. A composition comprising acrylonitrile and (a) a hydroxylamine having the formula

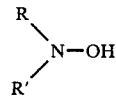

wherein R and R' are the same or different and are hydrogen, alkyl, aryl, alkaryl or aralkyl groups and (b) a para-phenylenediamine having the formula

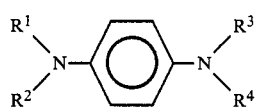

wherein $R^1$, $R^2$, $R^3$ and $R^4$ are the same or different and are hydrogen, alkyl, aryl, alkaryl, or aralkyl groups with the proviso that at least one of $R^1$, $R^2$ $R^3$, or $R^4$ is hydrogen, wherein: the alkyl, aryl, alkaryl and aralkyl groups have one to about twenty carbon atoms; the total amount of the hydroxylamine and the phenylenediamine is from about 1 ppm to about 10,000 ppm based upon the weight of the acrylonitrile; and the molar ratio of the hydroxylamine to the phenylenediamine is about 1:10 to about 10:1.

5. The composition according to claim 4 wherein the hydroxylamine is selected from the group consisting of N,N-diethylhydroxylamine, N,N-dibenzylhydroxylamine, methylbenzylhydroxylamine, and ethylbenzylhydroxylamine.

6. The composition according to claim 5 wherein the para-phenylenediamine is selected from the group consisting of N-phenyl-n'-(1,3-dimethylbutyl)-p-phenylenediamine, N-phenyl-N'-(1,4-dimethylpentyl)-p-phenylenediamine, and para-phenylenediamine wherein $R^1$, $R^2$, $R^3$ and $R^4$ are hydrogen.

* * * * *